United States Patent [19]

Lazzara et al.

[11] Patent Number: 4,856,994
[45] Date of Patent: Aug. 15, 1989

[54] PERIODONTAL RESTORATION COMPONENTS

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 148,056

[22] Filed: Jan. 25, 1988

[51] Int. Cl.[4] .............................................. A61C 8/00
[52] U.S. Cl. .................................... 433/173; 433/174
[58] Field of Search ............... 433/174, 173, 175, 176, 433/141

[56] References Cited

U.S. PATENT DOCUMENTS

| | | | |
|---|---|---|---|
| 3,576,074 | 4/1971 | Gault | 433/175 |
| 4,253,833 | 3/1981 | Edelman | 433/173 |
| 4,439,152 | 3/1984 | Small | 433/174 |
| 4,552,532 | 11/1985 | Mozsary | 433/174 |
| 4,588,381 | 5/1986 | Caracciolo | 433/173 |
| 4,722,688 | 2/1988 | Lonca | 433/173 |
| 4,723,913 | 2/1988 | Bergman | 433/173 |

Primary Examiner—John J. Wilson
Attorney, Agent, or Firm—Alfred H. Rosen

[57] ABSTRACT

A healing cap for use in the second stage of dental implantology covers the implanted prosthesis and shields its upper surface from overgrowth of gum tissue, and at the same time maintains an opening through the fleshy gum tissue that overlies the implant. This cap is shown to be useful without as well as with an intervening transmucosal abutment. A unique holder/driver enables the healing cap to be located and fixed in place in remotely accessible places in the mouth with minimal requirement for manual dexterity.

5 Claims, 2 Drawing Sheets

PERIODONTAL RESTORATION COMPONENTS

This invention relates in general to the dental field of prosthodontic restoration. More particularly it relates to dental implant systems in which an object substituting for a natural tooth root is surgically implanted in edentulous bone of the alveolar arches of the jaws. Such objects are now commonly known as dental implants, and the increasing use of them has given rise to a new dental field becoming known as "implantology".

Implantology is extending the scope of prosthodontic restoration to edentulous patients who formerly were limited to using removable bridges (ie: "false teeth"). After one or more dental implants has or have been successfully implanted, usually by an oral surgeon, or by a periodontist, in the jawbone(s) of a patient, the prosthodontist has the task of fashioning one or more prosthodontic restoration(s) and attaching it or them to the implants in a way that will provide a restoration that is not only anatomically and structurally adequate, and dentally functional, but also cosmetically attractive. The first stage in this process, that of implanting one or more biocompatible devices in the patient's jawbone(s) and achieving osseointegration between the implanted devices and the host bone structure, requires that after the surgical implanting has been done the implanted devices be left in place for a "healing" period of several months in order to allow osseointegration to take place.

The gum tissue is surgically closed at the end of the surgical implanting procedure, and remains closed during this healing period. It is reopened surgically when the healing period is deemed to be at an end, and if the implanted device is found to be soundly osseointegrated the prosthodontist can begin to design and make a dental restoration. This is stage two, and in this stage a need arises to provide to the prosthodontist an increasingly-wide variety of components which are needed to enable dental restorations to be designed by the prosthodontist and fabricated in laboratories, which are useful to support transitional denture during the time when permanent restorations are being prepared and when the patient's underlying gum and remaining tooth structure (if any) are being prophylactically prepared to receive new permanent restorative denture, and which will form links between the patient's dental implants and new restorative denture.

The invention is useful in implant systems where a transmucosal abutment is fixed to the top of an implant, as by an abutment screw, as well as systems which may not use a transmucosal abutment.

The components with which this invention is concerned are very small in size, only a little bit larger than the parts of a watch. Thus, for example, the invention provides a healing cap for use in stage two to cover an implant or a transmucosal abutment after the gum has been opened, and to preserve an opening through the gum after the first and subsequent visits to the prosthodontist. This cap is generally cylindrical, about two to five mm. in diameter, and has an axial length (together with the length of a transmucosal abutment if the latter is present ) equal approximately to the thickness of the patient's gum covering the alveolar arch over the implant area, about 2.5 mm. in one example. The implant, or the abutment screw, may have an internally threaded bore through which restored denture eventually will be attached to the implant, in which case the cap has an externally threaded screw post, and the cap is screwed onto the implant (via the abutment screw if present) so that it will extend through the gum and may have an outer surface lying flush with or above the outer surface of the gum when that is done. The task of manipulating this very small cap to install it is a delicate one, which risks dropping the cap in the patient's mouth. This invention teaches the design and use of a special holder-driver which, despite its necessarily-small size, enables the prosthodontist to hold the cap, put it into its desired location, and screw it fast to the implant, all with reliable dexterity, and greatly reduce the risk of losing it down the patient's throat.

When a healing cap according to the invention is used to cover the implant and to maintain an access opening through the overlying gum, it allows the gum tissue to heal against the side walls of the cap, which permits the tissue to heal at a particular height, and prevents tissue proliferation over the implant, or over the transmucosal abutment when the latter is present. It also protects the screw opening into the implant or the abutment screw for the gold screw that will be used in the next stage for mounting and supporting the patient's new denture.

The healing cap of the invention can be extended supragingivally to provide temporary retention for a relined over-denture, for example, when the prosthodontist is satisfied that the underlying implant is strong enough to support temporary denture. Until then, the healing cap without supragingival extension can be used without risk of stressing the underlying dental implant. The invention also provides a healing cap with supragingival extension sufficient to form an abutment head post for cemented prosthesis, thus giving the prosthodontist a wide variety of choices.

For the case where, owing to surgical conditions, two or more implants cannot be installed with a degree of parallelism that will be required by the prosthodontist, the invention provides a healing cap with a bendable supragingival extension.

These and other objects and features of the invention will become apparent from the following description of exemplary embodiments of the invention. This description refers to the accompanying drawings, in which.

Figure 1:
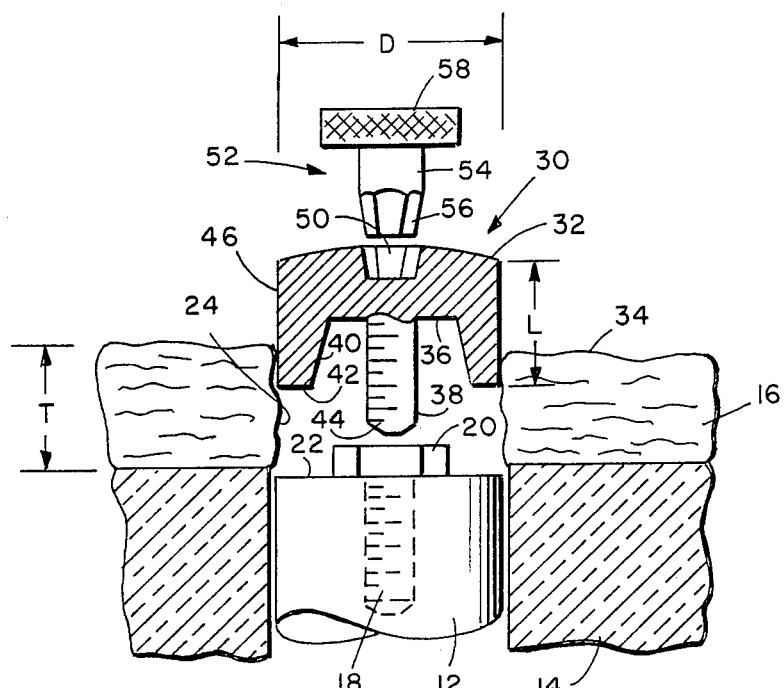
FIG. 1 is an exploded partial view, in longitudinal section, showing a healing cap according to the invention in relation to the environment in which it is intended to be used without a transmucosal abutment.

In FIG. 1 the top portion 12 of a dental implant 10 (see FIG. 6) is shown installed in a jaw-bone 14 covered with gum tissue 16. An internally-threaded bore 18 in the implant opens to the gum, where a hexagonal fitting 20 is provided at the top surface 22 of the implant. The implant 10 thus-far described is one of several that are now commercially available. Normal procedure with this kind of implant is to install the implant, close the bore 18 and allow the gum tissue to grow over it while osseointegration is permitted to take place. Later, preparatory to beginning prosthodontic restoration, the gum tissue is opened surgically to gain access to the implant. The present invention provides, among other things, a means to preserve an opening 24 in the gum tissue during prosthodontic procedures.

The healing cap 30 has a diameter "D" substantially identical to that of the top portion 12 of the implant, and an axial length "L" which is approximately the same as the thickness "T" of the gum tissue 16 overlying the jaw-bone 14 around the implant. To accomodate different gum thicknesses healing caps 30 are made in a variety of lengths "L", among which the prosthodontist may choose. The upper surface 32 of the healing cap, here shown slightly convex, is intended to be substantially flush with, or it may extend slightly outside of, the outer surface 34 of the surrounding gum when the healing cap is fully installed on the implant. The under side 36 of the cap is re-entrantly shaped to provide a cavity 38 surrounded by an annular skirt 40 terminating in an annular meeting surface 42. A threaded post 44 extends axially from the center of the cavity 38 outwardly beyond the annular meeting surface 42. To install the healing cap on the implant the post 44 is threaded into the bore 18 until the annular meeting surface 42 is brought into contact with the top surface 22 of the implant, when the cavity 38 acting together with the top surface 42 forms an enclosure protecting the fitting 20. The side surface 46 of the healing cap provide a wall against which the gum tissue can heal in the shape of the opening 24. The meeting surface 42 is in tight contact with the implant top surface 22, so that gum tissue does not proliferate over the implant. The upper surface 32 of the healing cap is approximately flush with or extends slightly beyond the outer surface 34 of the gum, so that gum tissue will not easily grow over the healing cap, but, at the same time, the healing cap does not project very far out of the gum, thereby minimizing the risk that the implant will be disturbed if the prosthodontist or the periodontist desires that osseointegration should proceed further.

The healing cap 30 is so small that the task of installing it may require a greater degree of manual dexterity than most persons possess, particularly if the implant is installed in a posterior location. A non-circular manipulation socket 50 is provided through the top surface 32 of the cap, and an axially-short driver 52 is provided to engage in this socket to turn the cap into the bore 18. It is known to use a hexagonal socket and a hexagonal ("Allen") wrench for this purpose. As is shown in FIG. 1, in the present invention the socket 50 is tapered in cross-section from wider at the top surface 32 to narrower within the body of the cap 30. Correspondingly, the driver 52 has a shank 54 fitted with a matching the socket 50, the bit being tapered from narrower at its tip extremity to wider toward the shank. The bit 56 is thus smaller at its tip than the opening into the socket 50, for facilitating entrance of the bit into the socket. At the same time, the taper of the bit and the socket is sufficiently gradual that when the driver 52 is pressed into the socket 50 the bit 56 can be engaged frictionally with the side-walls of the socket. To this end, the length of the bit is less than the depth of the socket, so that the bit will not bottom in the socket before the desired frictional engagement can be made. The cap 30 will then be retained by the driver 52 with a "wedging" engagement, and the two can be held and manipulated as a unit by the driver handle 58. The driver 52 then functions as a holder-driver, which enables a person with relatively ordinary dexterity to locate and install the cap on an implant, even in a posterior location, using a short holderdriver, as shown.

Once the cap has been installed, the driver can easily be disengaged by pulling enough to overcome the frictional contact between the conically-mated surfaces of the bit and the socket. For these purposes of the invention, a taper of 0.001 inch over an axial socket depth or bit length of 0.035 inch is useful.

The components shown in FIGS. 2, 3, 4 and 5 preserve the advantages of the healing cap 30 when the latter is not in use. Each of those components has a main body cap portion 30' with the same understructure as the healing cap, namely, the tissue boundary wall 46 of axial length "L", the annular meeting surface 42, the screw post 44, and the diameter "D", as the healing cap 30. Thus, when one of these components is used later in the restoration procedure, the healing process of the gum tissue will not be adversely affected.

Figures 2, 3, 4:
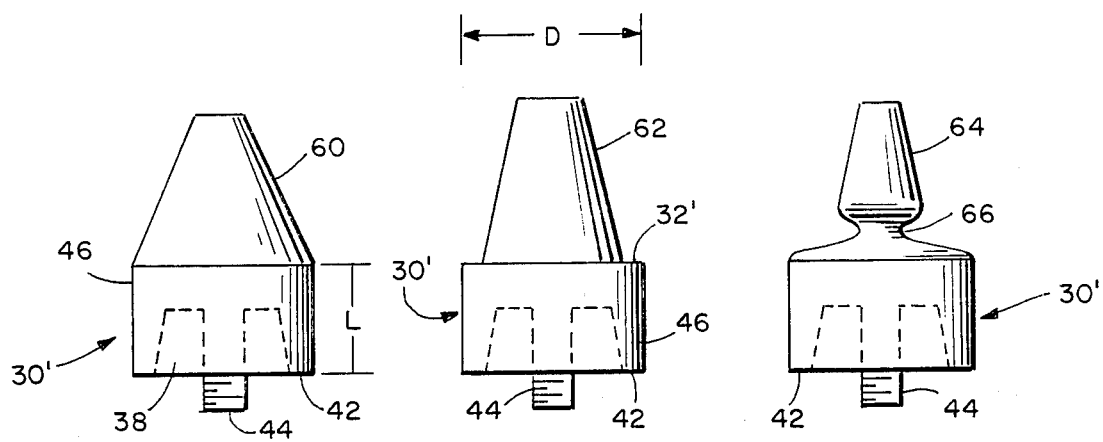
FIG. 2 is a side view of a healing cap extended supragingivally to provide an abutment head post.
FIG. 3 is a modification of FIG. 2.
FIG. 4 shows a healing cap fitted with an axially-bendable supragingival extension.

In FIG. 2, the component shown has a supragingivally-extending part 60 which may be used as an abutment head post for cemented prosthesis. In FIG. 3, the component shown has a supragingivally extending part 62 which tapers to a size, where it meets the top of the cap portion 30', which has a smaller diameter than the diameter "D" of the cap portion, leaving an annular shelf 32' at the top of the cap portion. This is useful in cases where a horizontal abutment is desired for a prosthesis.

The embodiment shown in FIG. 4 addresses the problem of parallelism. Here a supragingivally-extending portion 64 is attached to the main body of the cap portion 30' with a connecting portion 66 having a substantially reduced cross-sectional diameter, to provide for flexion of the supragingivally-extending portion away from the cylindrical axis of the main body of the cap portion.

Figures 5, 6:
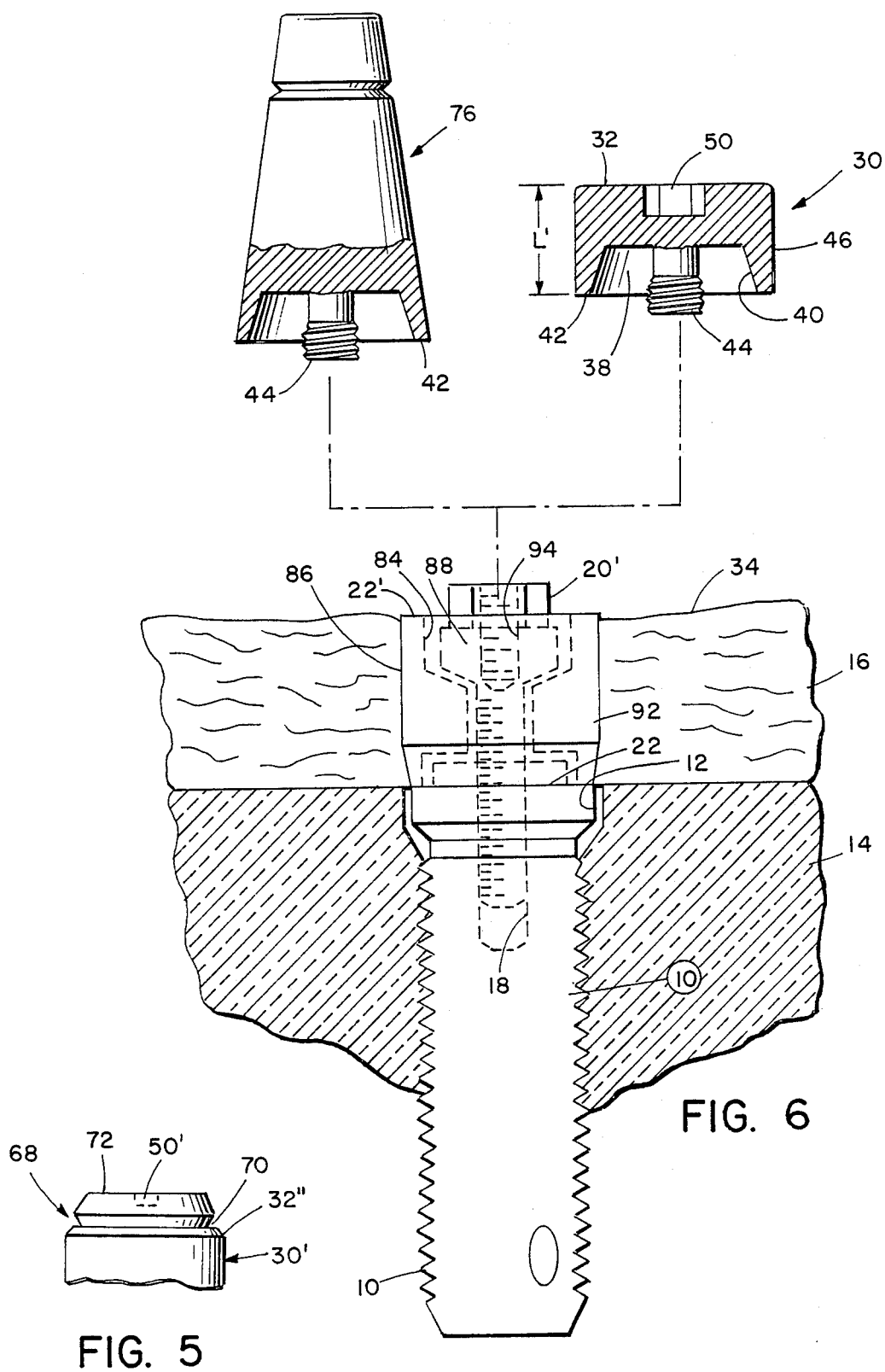
FIG. 5 is a partial view showing the healing cap modified for supporting a reline over-denture.
FIG. 6 is a partially-schematic view showing a dental implant fitted with a transmucosal abutment as it may be fitted alternatively with a healing cap according to the invention, or an abutment post.

FIG. 5 shows a temporary retention component, useful to help in retention of transitional denture lined with soft reline material. The main body 30' of the healing cap is fitted at its top, beyond the plane of the top surface 32", with a flattened extension 68 having an annular reentrant groove 70 and a flat top surface 72. The axial length of this extension 68 may be a fraction of or a bit longer than the length "L". This component will permit a patient to retain old dentition relined with soft reline material, as an alternative to no dentition at all, on a temporary basis. A socket 50', like the socket 50 in FIG. 1, is provided through the surface 72, for similar cooperative use with the holder-driver 52.

FIG. 6 shows a dental implant system in which, in stage two, the implant 10 is fitted with a transmucosal abutment 92. This abutment is fixed to the implant 10 with an abutment screw 88 which engages in the threaded bore 18, and has at its top a fitting 22' similar to the fitting 22 of the implant 10. A threaded bore 94 extends axially into the abutment screw from an opening in the center of the fitting 22'. The side walls 86 of the abutment 92 serve, in part, to define the opening 24, through the gum tissue. The abutment screw 88 has a head which fits loosely in a recess 84 in the top of the abutment. An annular top surface 22' of the abutment surrounds this recess.

For the system illustrated in FIG. 6, the healing cap 30 has a length "L" which, when added to the axial length of the transmucosal abutment 92, will provide the desired location of the outer surface 32 of the cap, relative to the outer surface 34 of the gum tissue. Healing caps intended for use in the system of FIG. 6 may, therefore, be considerably shorter than the healing caps intended for use in the system of FIG. 1, and this difference adds urgency to use of the improved holder-driver 52, to which end the socket 50 shown in FIG. 6 is tapered as in FIG. 1. The screw post 44 is engaged in the bore 94 of the abutment screw. Owing to the presence of the abutment 92, the system of FIG. 6 may use other components, such as the post 76, which have little or none of the cylindrical side walls 46.

We claim:

1. In combination, an auxiliary component for a dental device implanted in bone of a patient's jaw, said implanted device having a gingivally-oriented terminating surface, and an opening through said terminating surface into a bore extending axially into said device for receiving a prosthodontic restoration, said auxiliary component having at a first end a post extending from said component for engaging in said bore, said auxiliary component having an outer surface at a second end opposite said first end, and a non-circular manipulating socket opening through said outer surface into said auxiliary component, said socket tapering in cross-section from wider at said outer surface to narrower within said auxiliary component, and a manipulating tool having a shank fitted with a bit of non-circular cross-section substantially matching the cross-section of said socket, said bit being tapered similarly to the taper in cross-section of said socket from a narrower portion at its extremity having a cross-sectional dimension similar to the narrower portion of said socket, to a wider portion toward said shank having cross-sectional dimensions similar to the wider opening into said socket, for facilitating the entrance of said bit into said socket and frictionally engaging said bit in said socket.

2. A combination according to claim 1 in which said socket tapers about 0.001 inch over an axial depth of about 0.035 inch, and said bit tapers about 0.001 inch over an axial length not greater than about 0.035 inch.

3. A combination according to claim 2 in which said axial length is less than said axial depth.

4. An auxiliary component according to claim 1, having a transversely-flattened portion extending supragingivally for providing temporary retention of an overdenture lined with a soft material, said second portion including radially-oriented physical retention means for cooperating retentively with said soft reline material.

5. An auxiliary component according to claim 1 in which said outer surface is convex.

* * * * *